United States Patent
Bobroff (10) Patent No.: US 8,409,125 B2
(45) Date of Patent: Apr. 2, 2013

(54) ADAPTABLE PERIOPERATIVE CELL-SALVAGE SYSTEM AND METHODS AND DISPOSABLE UNITS FOR SAME

(75) Inventor: Alec D. Bobroff, Norfolk, MA (US)

(73) Assignee: Haemonetics Corporation, Braintree, MA (US)

( * ) Notice: Subject to any disclaimer, the term of this patent is extended or adjusted under 35 U.S.C. 154(b) by 737 days.

(21) Appl. No.: 11/936,595

(22) Filed: Nov. 7, 2007

(65) Prior Publication Data
US 2008/0108931 A1 May 8, 2008

Related U.S. Application Data

(60) Provisional application No. 60/864,905, filed on Nov. 8, 2006.

(51) Int. Cl.
*A61M 37/00* (2006.01)
(52) U.S. Cl. ............... 604/6.01; 604/6.15; 604/4.01
(58) Field of Classification Search ............ 604/4.01, 604/6.02, 6.1, 6.15; 494/43
See application file for complete search history.

(56) References Cited

U.S. PATENT DOCUMENTS

| | | | | |
|---|---|---|---|---|
| 4,668,214 A * | 5/1987 | Reeder | ............. | 494/37 |
| 4,680,025 A * | 7/1987 | Kruger et al. | ............. | 604/6.04 |
| 4,828,543 A | 5/1989 | Weiss et al. | ............. | 604/4 |
| 5,234,403 A * | 8/1993 | Yoda et al. | ............. | 604/6.09 |
| 5,298,016 A * | 3/1994 | Gordon | ............. | 604/5.01 |
| 5,417,650 A * | 5/1995 | Gordon | ............. | 604/5.04 |
| 5,464,399 A * | 11/1995 | Boettger | ............. | 604/533 |
| 5,554,293 A * | 9/1996 | Uhoch | ............. | 210/650 |
| 5,634,893 A * | 6/1997 | Rishton | ............. | 604/6.1 |
| 5,651,766 A | 7/1997 | Kingsley et al. | ............. | 604/6 |
| 5,658,256 A * | 8/1997 | Shields | ............. | 604/192 |
| 5,733,253 A | 3/1998 | Headley et al. | ............. | 604/4 |
| 5,891,080 A * | 4/1999 | Skinkle et al. | ............. | 604/6.11 |
| 5,954,971 A * | 9/1999 | Pages et al. | ............. | 210/739 |
| 6,007,472 A * | 12/1999 | Schill et al. | ............. | 494/41 |
| 6,251,284 B1 * | 6/2001 | Bischof et al. | ............. | 210/739 |
| 6,251,291 B1 | 6/2001 | Lamphere et al. | ............. | 210/767 |
| 6,508,778 B1 * | 1/2003 | Verkaart et al. | ............. | 604/6.15 |
| 6,632,189 B1 * | 10/2003 | Fallen et al. | ............. | 604/4.01 |
| 6,632,191 B1 * | 10/2003 | Headley et al. | ............. | 604/6.01 |
| 6,723,086 B2 * | 4/2004 | Bassuk et al. | ............. | 604/890.1 |
| 6,800,072 B2 * | 10/2004 | Patzer | ............. | 604/260 |

(Continued)

FOREIGN PATENT DOCUMENTS

EP 0 223 126 A2 5/1987
EP 0223126 5/1987
(Continued)

OTHER PUBLICATIONS

Colder Products Company Quick Couplings & Fittings for Plastic Tubing catalog, 2011.*

(Continued)

*Primary Examiner* — Susan Su
(74) *Attorney, Agent, or Firm* — Sunstein Kann Murphy & Timbers LLP (57) ABSTRACT

A blood-collection system configured to permit selection of either collection and disposal of shed blood from a patient or collection and processing of shed blood for autologous transfusion back to the patient includes an automated blood-processing machine. The system may also include a blood-collection reservoir, a separation chamber, and a fluid conduit. The blood-collection reservoir may be engageable with the blood-processing machine so that the machine can identify and report the presence of blood in the reservoir. The separation chamber may also be engageable with the blood processing machine. The fluid conduit may be configured to selectively join the reservoir to the separation chamber by a quick-connect coupling.

13 Claims, 5 Drawing Sheets

U.S. PATENT DOCUMENTS

| | | | |
|---|---|---|---|
| 6,890,316 B2 * | 5/2005 | Rawles et al. | 604/6.16 |
| 2005/0203469 A1 | 9/2005 | Bobroff et al. | 604/318 |

FOREIGN PATENT DOCUMENTS

| | | |
|---|---|---|
| EP | 0682953 | 11/1995 |
| EP | 1166806 | 1/2002 |
| JP | 62-120857 A | 6/1987 |
| JP | 2-502522 A | 8/1990 |
| JP | 08-506982 A | 7/1996 |
| JP | 11-506030 A | 6/1999 |
| JP | 2001-017540 | 1/2001 |
| JP | 2002-533166 | 10/2002 |
| JP | 2008-538514 | 10/2008 |
| WO | 84/00892 A1 | 3/1984 |
| WO | WO 84/00892 | 3/1984 |
| WO | 94/21311 A2 | 9/1994 |
| WO | 96/40319 A1 | 12/1996 |
| WO | WO 96/40319 | 12/1996 |
| WO | 98/14163 A1 | 4/1998 |
| WO | 00/38756 | 7/2000 |
| WO | 2006/100651 A1 | 9/2006 |

OTHER PUBLICATIONS

International Searching Authority, International Search Report—International Application No. PCT/US2007/083957, dated Apr. 24, 2008, together with the Written Opinion of the International Searching Authority, 12 pages.

* cited by examiner

FIG. 1

PRIOR ART

ADAPTABLE PERIOPERATIVE CELL-SALVAGE SYSTEM AND METHODS AND DISPOSABLE UNITS FOR SAME

PRIORITY

This patent application claims priority from the following provisional U.S. patent applications:

Application No. 60/864,905, filed Nov. 8, 2006, entitled, "Adaptable Perioperative Cell-Salvage System and Methods and Disposable Units form Same,", and naming Alec D. Bobroff as inventor, the disclosure of which is incorporated herein, in its entirety by reference.

TECHNICAL FIELD

The present invention relates to blood-processing systems, particularly those systems that process blood collected during or after surgery, as well as to disposable units used in such systems and to methods of using such systems.

BACKGROUND ART

Prior-art systems for salvaging blood from surgical sites and wound drains often employ disposable units that include a reservoir for collecting the blood-containing fluid and a separation device (such as a centrifuge bowl or disk) for separating out and washing the red blood cells (RBCs). The RBCs salvaged using these systems may be autotransfused back into the patient, thereby reducing the need for allogenic blood transfusions. Examples of such blood-salvage systems include those described in U.S. Pat. No. 6,251,291 to Lamphere et al., issued Jun. 26, 2001, and in U.S. Patent Application Publication No. 2005/0203469 by Bobroff et al., published Sep. 15, 2005. Both this patent and published application are incorporated herein by reference. Commercial examples of such systems include the OrthoPAT® Surgical Blood Salvage System and the CardioPAT™ Surgical Blood Salvage System, both of which are sold by Haemonetics Corporation of Braintree, Mass.

Figure 1:
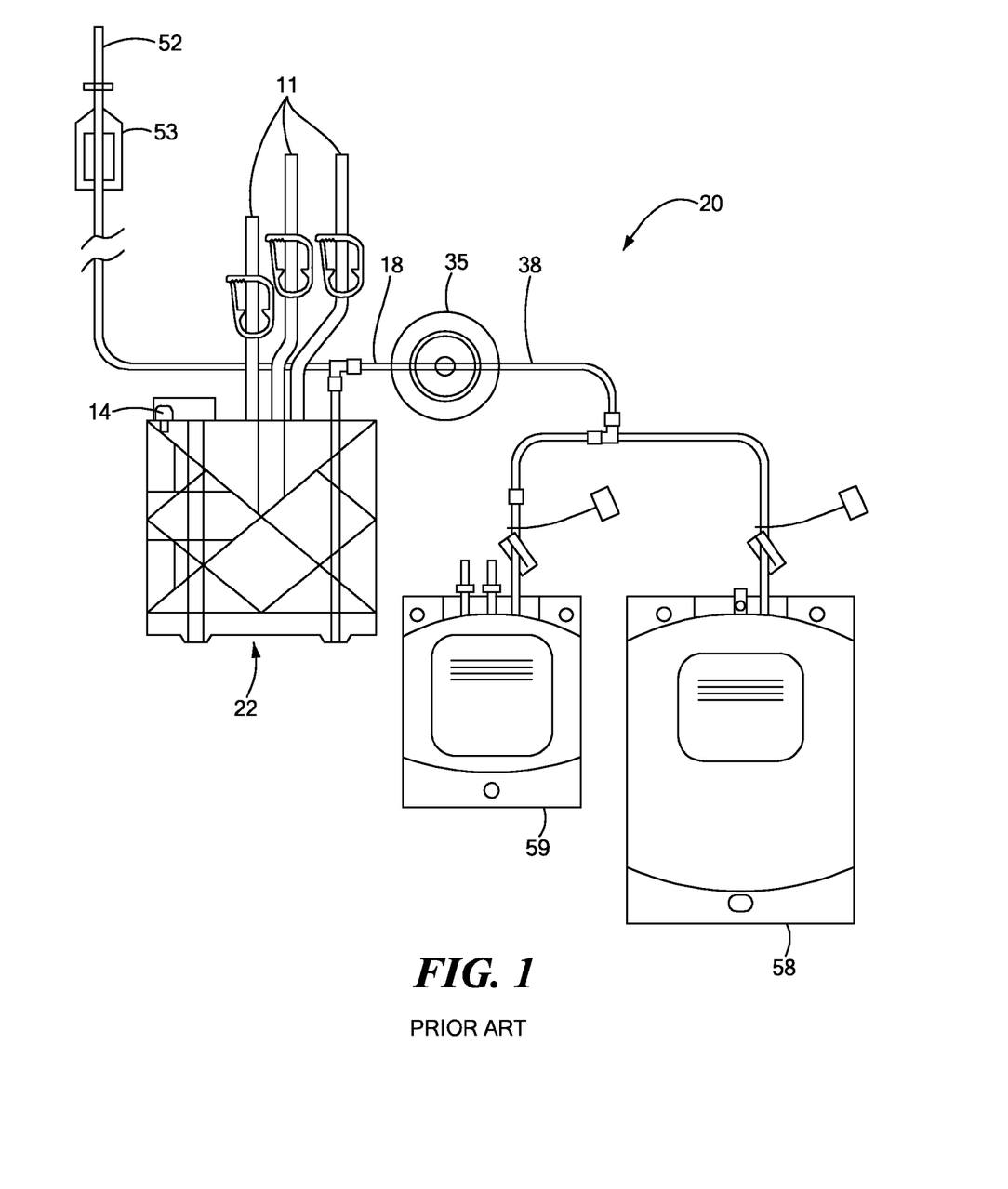
FIG. 1 shows a prior-art disposable set used in an intraoperative blood-salvage system.

FIG. 1 shows a disposable set 20 that may be used in a prior-art cell-salvage systems used during surgery. The set 20 includes a centrifuge disk 35 connected to an inlet tube 18 and an outlet tube 38. The inlet tube 18 is connected to a reservoir 22 for collecting the blood and other fluids from a surgical site. The inlet tube 18 forms a permanent connection between the reservoir 22 and the centrifuge disk 35. This reservoir may be of the type described in U.S. Pat. No. 6,251,291, referred to above. The reservoir 22 includes port lines 11, through which the blood and other fluids are collected from the surgical site, and a vacuum inlet port 14, through which a partial vacuum is provided to the reservoir for drawing the blood and other fluids through the port lines. The inlet tube 18 is also connected to a saline air-elimination filter 53 and a saline spike 52, which may be connected to a source of saline, which may be used during the washing of the RBCs in the centrifuge disk 35. The outlet tube 38 is connected to an RBC bag 59 and a waste bag 58.

Blood and other fluids are suctioned from a surgical site and drawn into the reservoir 22. These fluids are drawn from the reservoir 22 into the centrifuge disk 35, which is then spun so as to separate out the RBCs from the plasma and other fluids. The plasma and other fluids may be directed to the waste bag 58. The RBCs may then be washed in the centrifuge disk 35 with saline from the saline source. After washing, the saline may be separated from the RBCs and directed to the waste bag 58, and the washed RBCs directed to the RBC bag 59. The RBCs may then be retransfused to into the patient.

Often the amount of blood collected in the reservoir is insufficient to carry out the separation and wash procedures. In such a situation, because the reservoir and separation chamber are permanently connected by tube 18, the entire disposable set 20 must be discarded after the procedure, even though the centrifuge disk 35, the RBC bag 59 and waste bag 58 are not utilized. Discarding the entire disposable even though the separation chamber is unused is wasteful and adds unnecessary expense to surgical procedures that ultimately do not lead to washing and reinfusing of blood to the patient.

SUMMARY OF THE INVENTION

In various embodiments of the invention, an adaptable system is provided so that certain disposable components of the system do not need to be discarded if they are not utilized.

In one embodiment of the invention, a blood-collection system is configured to permit selection of either (a) collection and disposal of shed blood from a patient or (b) collection and processing of shed blood for autologous transfusion back to the patient. The system includes an automated blood-processing machine, a blood-collection reservoir engageable with the blood-processing machine so that the machine can identify and report the presence of blood in the reservoir, a separation chamber engageable with the blood-processing machine, and a fluid conduit configured to selectively join the reservoir to the separation chamber by a quick-connect coupling.

In another embodiment, a first disposable-set component is provided for use in a blood-salvage system. The first disposable set preferably includes a reservoir for collecting shed blood, a collection port for permitting shed blood to be drawn from a site into the reservoir, an outlet port for permitting blood to be drawn from the reservoir, and a quick-connect coupling for connecting the outlet port to a separation chamber. The reservoir, collection port, outlet port and coupling are preferably stored in a hermetically sealed package separate from the separation chamber. The reservoir may include a vacuum port for connecting the reservoir to a vacuum source, so as to provide a vacuum to draw shed blood into the reservoir from a surgical site or wound drain.

In another embodiment, a second disposable-set component is provided for use in the blood-salvage system. The second disposable-set component includes a separation chamber, where a blood component (preferably RBCs) may be separated from other fluids, and a quick-connect coupling for connecting the separation chamber to the collection reservoir's coupling. The separation chamber is stored in a separate hermetically sealed package from the collection reservoir. The second disposable-set component may also include a blood-component container for receiving the separated blood component from the separation chamber, and/or a waste container for receiving waste fluids from the separation chamber. These containers may be stored in the same hermetically sealed package as the separation chamber.

In another embodiment, a method for salvaging blood includes the steps of (i) removing the first disposable-set component from its hermetically sealed package, (ii) collecting a volume shed blood in the reservoir of the first disposable-set component, (iii) monitoring the volume of shed blood in the reservoir, and if the volume of shed blood reaches a threshold, performing the following additional steps: (iv) removing the second disposable set component from its hermetically sealed package, (v) connecting the first disposable set component's coupling to the second disposable set's coupling, (vi) drawing shed blood from the reservoir into the separation chamber of the second disposable-set component, and (vii) separating a blood component from other fluids in the separation chamber.

In another embodiment, a method for collecting shed blood from a patient into a disposable reservoir, while maintaining the option of processing the shed blood in a disposable separation chamber for autologous transfusion back to the patient, includes providing an automated blood-processing machine, a blood-collection reservoir engageable with the blood-processing machine so that the machine can identify and report the presence of blood in the reservoir, a separation chamber engageable with the blood-processing machine, and a fluid conduit configured to selectively join the reservoir to the separation chamber by a quick-connect coupling; collecting blood from a patient into the reservoir and operating the machine to monitor the amount of blood collected; joining the separation chamber to the reservoir by securing the quick-connect coupling in the conduit; transferring blood from the reservoir to the separation chamber; operating the processing machine to separate unwanted material from the blood to provide cleaned blood; and returning the cleaned blood to the patient.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

"Perioperative," as used herein, describes a product or method used during or shortly after surgery. This term includes the intraoperative suctioning of blood (along with other fluids, such as an irrigant solution) from surgical sites and the postoperative collection of blood from a wound drain.

"Intraoperative blood salvage," as used herein, describes a system where shed blood is collected during surgery—typically by being suctioned from a surgical site. The separation of RBCs out of the shed blood collected intraoperatively, as well as the washing of the separated RBCs, may occur after the surgery is completed.

"Postoperative blood salvage," as used herein, describes a system where shed blood is collected after surgery typically from a wound drain.

It will be appreciated that the present invention may be adapted for use with either intraoperative or postoperative blood salvage or a combination of the two.

Figure 2:
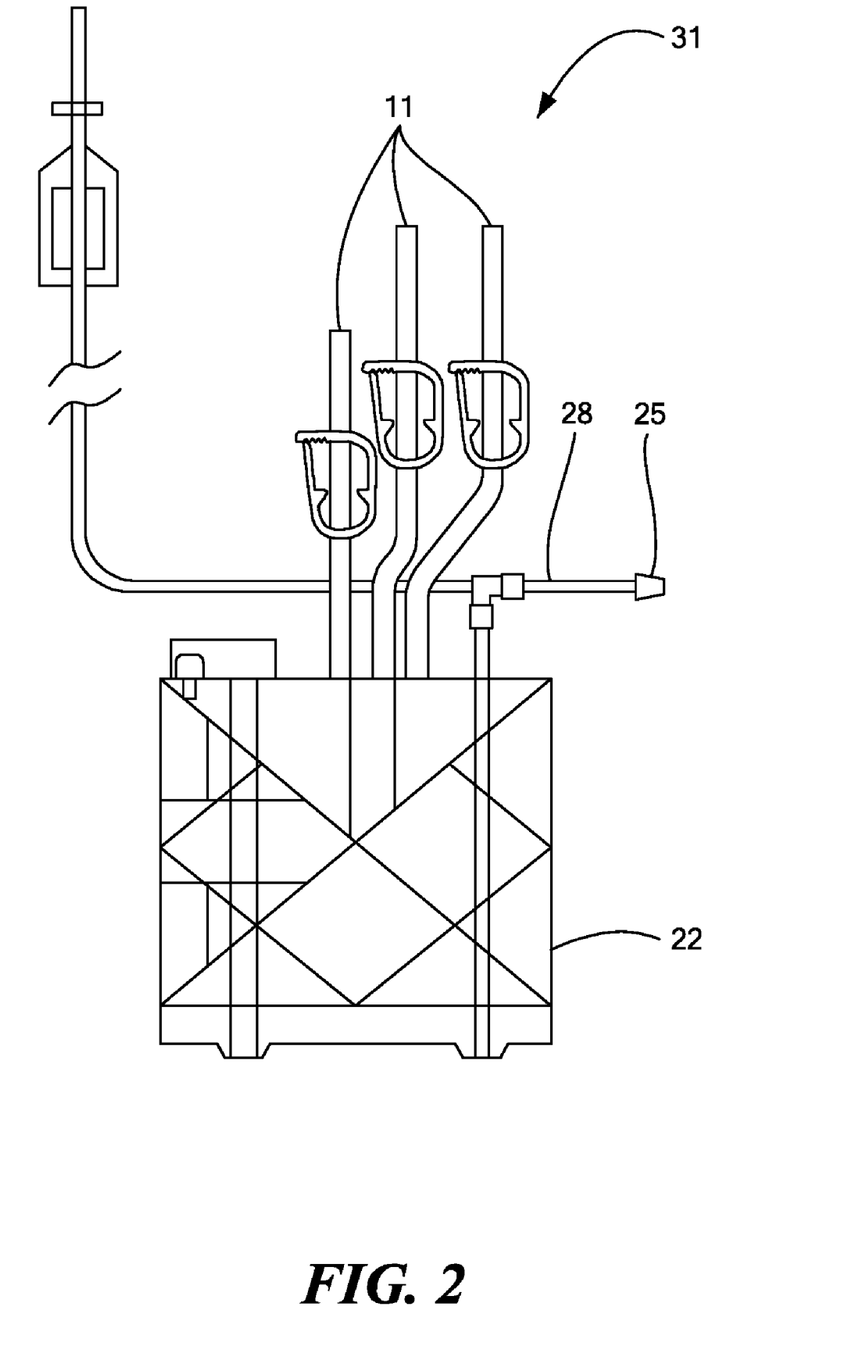
FIGS. 2 and 3 respectively show first and second disposable-set components according to a preferred embodiment of the invention.
Figure 3:
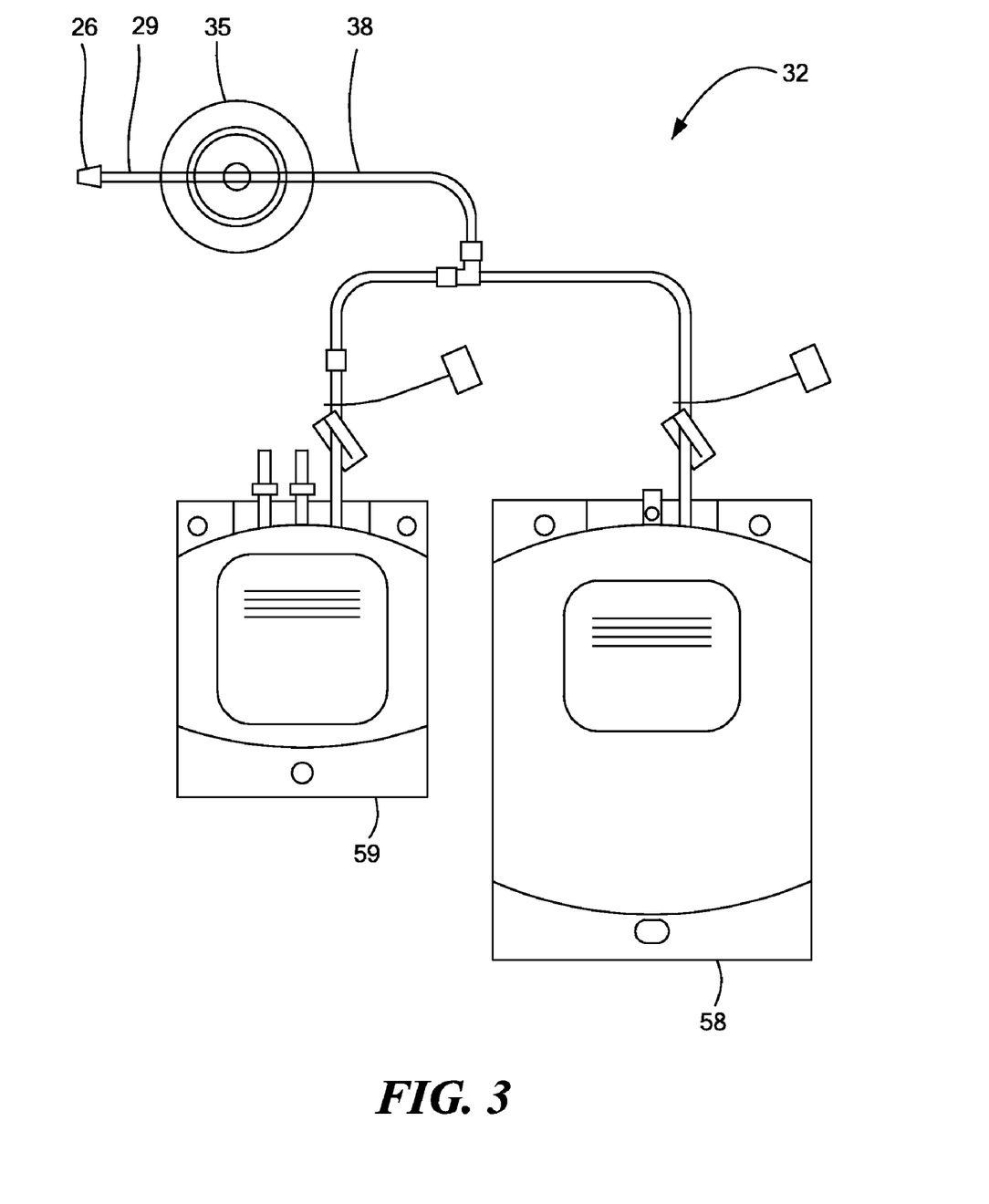

FIGS. 2 and 3 show two disposable-set components adapted from the prior-art disposable set of FIG. 1. FIG. 2 shows a first disposable-set component 31, which includes the reservoir 22, collection ports 11, an outlet tube 28, as well as other elements. The reservoir 22 may be of a design according to U.S. Pat. No. 6,251,291 (which, as noted above, is incorporated herein by reference). The outlet tube 28 includes a releasable coupling 25 for permitting releasable connection of the first disposable-set component 31 to the second disposable-set component 32 of FIG. 3. Preferably, the releasable coupling 25 is designed so as to not permit air into outlet tube 28, while the coupling 25 is unattached.

The second disposable-set component 32 includes the centrifuge disk 35, an inlet tube 29, a disk outlet tube 38, a RBC collection bag 59 and a waste bag 58 (as well as other elements, such as a valving mechanism). (The centrifuge disk 35 may be of the variable-volume design described in U.S. Pat. No. 5,733,253 issued Mar. 31, 1998 to Headley et al. and in U.S. Pat. No. 5,651,766 issued Jul. 29, 1997 to Kingsley et al.—both of which are incorporated herein by reference—although it will be appreciated that other types of separation chambers, such as centrifuge bowls, may also be used in the blood-salvage system of the present invention.) The inlet tube 29 includes a releasable coupling 26 designed to be easily and quickly connectable to the first disposable-unit component's releasable coupling 25. Preferably, the second disposable-set component's releasable coupling 26 may also be designed so as to not permit air into inlet tube 29, while the coupling 26 is unattached.

Couplings made by Colder Products Company of St. Paul, Minn.—in particular part nos. SMF0291 and SMM0291—may be used for the couplings 25 and 26.

Each of the first and second disposable-set components 31 and 32 are preferably stored in separate hermetically sealed containers. Thus, the first disposable-set component 31 is first removed from its hermetically sealed container and used in the collection of shed blood. Preferably, the second disposable-set component 32 is removed from its hermetically sealed container only if enough shed blood is collected in the reservoir 22 of the first disposable-set component to permit processing of the shed blood in the separation chamber to yield retransfusable RBCs.

Figure 4:
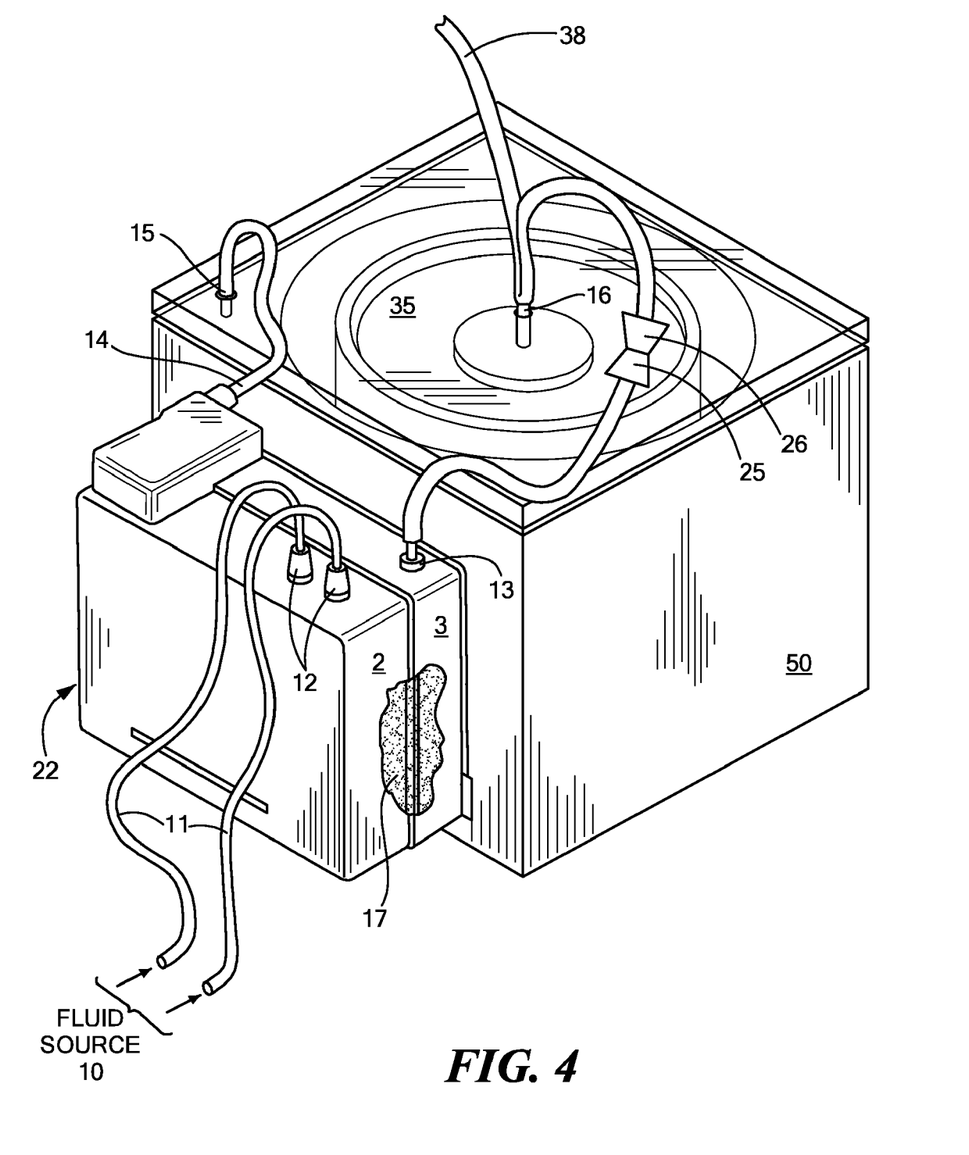
FIG. 4 shows first and second disposable-set components of an alternative embodiment mounted on and in a base unit.

FIG. 4 shows an alternative pair of disposable-set components that are connected to each other with couplings 25 and 26 and that are used with a base unit 50. The reservoir 22 is shown connected to base unit 50. Unfiltered fluid obtained from a fluid source 10 is directed into the reservoir 22 through unfiltered-fluid inlets 12. The fluid source 10 may be in communication with a surgical site where blood, debris, and other fluids are generated. During a surgical procedure, it may be critical that blood, as well as other fluids and debris, be expeditiously removed from the surgical site as quickly as such products evolve. The reservoir 22 is designed to efficiently collect and filter fluid from a range of procedures. A vacuum source 15 on the base unit 50 is connected to the reservoir 22 through vacuum port 14. A differential pressure is established causing fluid flow from the fluid source 10 into the reservoir 22. The base unit 50 may employ a partial vacuum to draw filtered shed blood from the system's filtrate outlet 13 and into the inlet 16 of a centrifuge disk 35. In this embodiment, the reservoir 22 is divided into an inlet cavity 2 and an adjacent outlet cavity 3. A filter member 17 is shown disposed so as to physically separate inlet cavity 2 from outlet cavity 3.

Initially, just the first disposable-set component including reservoir 22 is attached to the base unit 50. A dummy disk may be inserted in the base unit 50 if the software controlling the base unit requires that a disk be inserted into the base unit's chuck before shed blood can be collected. The amount of shed blood collected in the reservoir may be monitored by the base unit 50. (The procedure and base unit configuration described in U.S. Patent Application Publication No. 2005/0203469, which as noted above, is incorporated herein by reference, may be used to monitor the amount of shed blood collected in the reservoir in some embodiments of the present invention.)

Once the base unit 50 has determined that a sufficient amount of shed blood has been collected, the base unit provides to the operator an indication that a threshold volume has been collected. Upon this indication, several steps may take place: the second disposable-set component may be removed from its hermetically sealed container; the dummy disk may be removed from the base unit, so that the real centrifuge disk 35 can be inserted into the base unit 50; and the couplings 25 and 26 of the two disposable-unit components are connected to each other. At this point, shed blood may be transferred from the reservoir 22 into the centrifuge disk 35, and the shed blood may then be processed to yield RBCs, according to known procedures for salvaging RBCs. Waste products and the salvaged RBCs exit from the centrifuge disk 35 through outlet tube 38 to pass respectively to a waste bag and an RBC bag.

If the base unit does not detect that a sufficient volume of fluid has been collected, the second disposable-set component is not removed from its hermetically sealed container and thus can be saved for a subsequent procedure with a different patient. Thus, significant cost savings can be achieved if not enough shed blood is collected for a full salvage procedure. In addition, doctors can avoid guessing which procedures are and are not likely to generate a sufficient volume of shed blood so as to avoid wasting a full disposable set—like the one shown in FIG. 1—in procedures less likely to justify the use of a full disposable set. Instead, the doctors can simply use the first disposable-set component—like the one of FIG. 2—for all procedures, and if a sufficient volume is collected, the doctors can employ the second disposable-set component, like the one of FIG. 3. Thus, some patients can be spared the risks associated with allogenic blood transfusions if a procedure generates an unexpectedly high volume of shed blood. Thus, the present invention can help reduce costs while reducing risks for the patient.

Figure 5:
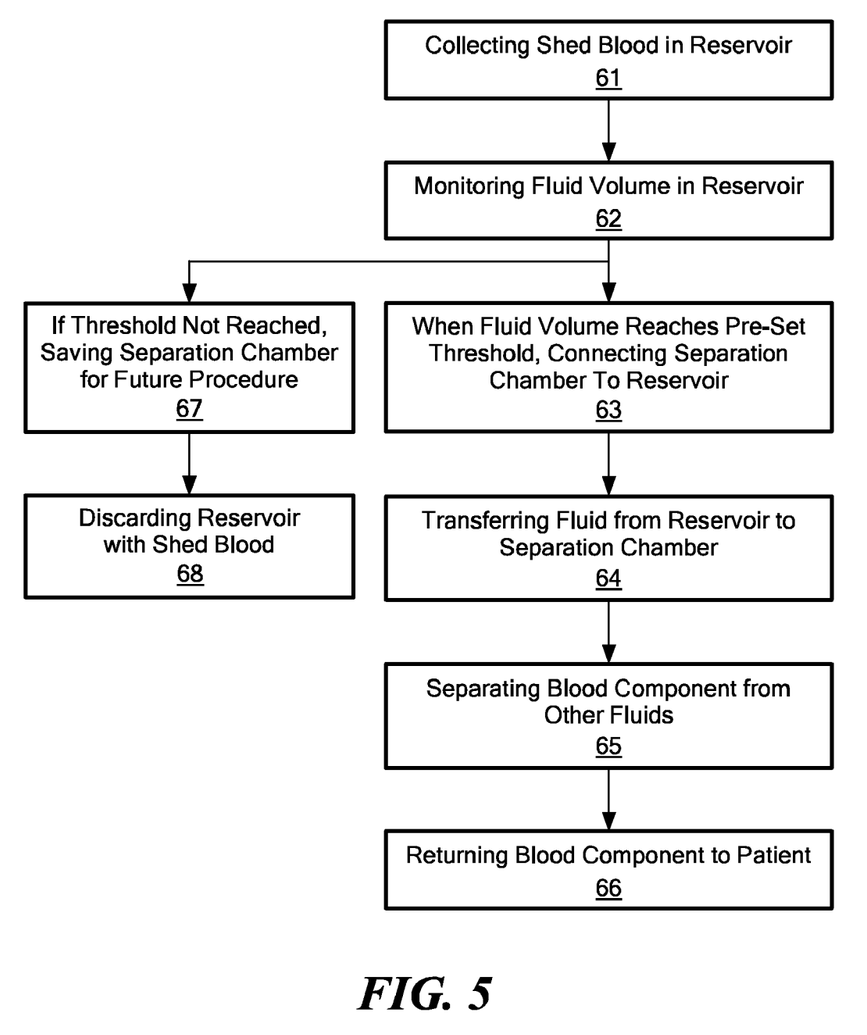
FIG. 5 shows a flow chart of a method according to one embodiment of the invention.

FIG. 5 is a flow chart showing the basic steps involved in a method according to one embodiment of the invention. In step 61, shed blood is collected (such as from a surgical site and/or a wound drain) in a reservoir. In step 62, the volume of fluid in the reservoir is monitored, preferably by a base unit to which the reservoir is attached. Preferably, the base unit can determine or estimate the actual amount of blood (as opposed to the total amount of all fluids) in the reservoir and use that information to determine whether the full salvaging procedure should proceed. Alternatively, the base unit can simply measure the total volume of all fluids in the reservoir, and make the determination about whether to proceed with the full salvaging procedure based on that information instead. The base unit can be configured to activate a visual or audible alarm when a set threshold value is reached.

In step 63, a threshold amount of fluid is collected in the reservoir, and at that point the separation chamber is attached to the reservoir. Up until this point, the separation chamber and other elements of the second disposable-unit component can be kept unused in its own hermetically sealed container. If the threshold amount of fluid is not collected during the procedure, the second disposable-unit component is saved for a future procedure (step 67) and the first disposable-set component is simply disposed of at the end of the current procedure (step 68). It is noted that the threshold amount of fluid needed in the reservoir to make processing worthwhile is determined by the healthcare professional on a case-by-case basis. The value may be preset into the base unit electronics or through the user interface. Various factors may considered such as patient size, volume of blood and fluid collected, hematocrit and others.

After the separation chamber is attached to the reservoir in step 63, fluid is transferred from the reservoir to the separation chamber (step 64). In step 65, a blood component—typically RBCs—is separated from the rest of the fluid in the separation chamber. This separation is preferably accomplished by the base unit spinning the separation chamber at a sufficiently high speed for a sufficient period of time. The blood component may optionally be washed with saline at this point. Preferably, after being separated and washed, the blood component is directed to a bag or other container, from which the blood component can be delivered back to the patient in step 66.

Although the above discussion discloses various exemplary embodiments of the invention, it should be apparent that those skilled in the art can make various modifications that will achieve some of the advantages of the invention without departing from the true scope of the invention.

What is claimed is:

1. A blood-salvage system comprising:
   a blood-processing machine attached to a reservoir for collecting shed blood, said blood-processing machine configured to receive and operate a centrifuge rotor in a blood separating and return mode, said blood-processing machine also configured to draw blood into the reservoir prior to receiving the centrifuge rotor; and
   a disposable-set component comprising:
      said reservoir, wherein the reservoir includes
         a collection port for permitting shed blood to be drawn from a site into the reservoir,
         an outlet port for permitting blood to be drawn from the reservoir via an outlet tube; and
         a first quick-connect coupling for connecting the outlet port and outlet tube to the centrifuge rotor, the first quick-connect coupling adapted to connect with a second quick-connect coupling connected to an inlet tube leading to the centrifuge rotor, the first quick-connect coupling preventing air from entering the outlet tube when disconnected from the second quick-connect coupling, the second quick-connect coupling preventing air from entering the inlet tube when disconnected from the first quick-connect coupling,
      wherein the reservoir and the coupling are stored in a separate hermetically sealed package from the centrifuge rotor.

2. A blood-salvage system according to claim 1, wherein the reservoir includes a vacuum port for connecting the reservoir to a vacuum source.

3. The blood-salvage system according to claim 1, wherein the blood-salvage system includes a dummy disk to allow the blood-salvage system to operate in the collection mode when the centrifuge rotor is not installed.

4. A blood-salvage system comprising:
   a disposable-set component comprising:
      a centrifuge rotor for separating a blood component from other fluids, and
      a first quick-connect coupling for connecting the centrifuge rotor to a collection reservoir via an inlet tube and an outlet tube, the first quick- connect coupling being connected to the inlet tube and adapted to connect with a second quick-connect coupling connected to the outlet tube leading to the collection reservoir, the first quick-connect coupling preventing air from entering the inlet tube when disconnected from the second quick- connect coupling, the second quick-connect coupling preventing air from entering the outlet tube when disconnected from the first quick-connect coupling, wherein the centrifuge rotor is stored in a separate hermetically sealed package from the collection reservoir; and a blood-processing machine configured to receive and operate the centrifuge rotor and also configured to draw blood into the collection reservoir prior to receiving the centrifuge rotor.

5. The blood-salvage system according to claim 4, further including a blood-component container for receiving the separated blood component from the centrifuge rotor, wherein the blood-component container is stored in the same hermetically sealed package as the centrifuge rotor.

6. The blood-salvage system according to claim 4, further including a waste container for receiving waste fluids from the centrifuge rotor, wherein the waste container is stored in the same hermetically sealed package as the centrifuge rotor.

7. The blood-salvage system according to claim 4, wherein the centrifuge rotor is a variable-volume centrifuge rotor.

8. The blood-salvage system according to claim 4, wherein the blood component is autotransfused into a patient 9. The blood-salvage system according to claim 4, wherein the blood component includes red blood cells.

10. A disposable-set component according to claim 4, wherein the blood-salvage system iincludes a dummy disk to allow the blood-salvage system to operate in the first configuration when the centrifuge rotor is not installed.

11. A blood-salvage system comprising:
a disposable set comprising:
a first disposable-set component having a reservoir for collecting shed blood, the reservoir including a collection port for permitting shed blood to be drawn from a site into the reservoir and an outlet port for permitting blood to be drawn from the reservoir via an outlet tube;
a second disposable-set component including a centrifuge rotor for separating a blood component from other fluids, the centrifuge rotor having an inlet port and an inlet tube for introducing blood into the centrifuge rotor;
a first quick-connect coupling connected to the outlet tube;
a second quick-connect coupling connected to the inlet tube and connectable to the first quick connect coupling to fluidly connect the first fluid disposable set and the second disposable set;
a first hermetically sealed package;
a second hermetically sealed package,
wherein the first quick-connect coupling prevents air from entering the outlet tube when disconnected from the second quick-connect coupling, and the second quick-connect coupling prevents air from entering the inlet tube when disconnected from the first quick-connect coupling, and wherein the centrifuge rotor is stored in the first hermetically sealed package and the collection reservoir is stored in the second hermetically sealed package; and
a blood-processing machine configured to receive and operate the centrifuge rotor and also configured to draw blood into the reservoir prior to receiving the centrifuge rotor.

12. A blood-salvage system according to claim 11, wherein the blood-salvage system includes a dummy disk to allow the blood-salvage system to operate in the collection mode when the centrifuge rotor is not installed.

13. A blood-salvage system according to claim 11, wherein the first quick-connect coupling and the second quick-connect coupling provide sensory feedback to a user upon connection.

* * * * *